(12) United States Patent
Bodor

(10) Patent No.: US 11,691,363 B2
(45) Date of Patent: Jul. 4, 2023

(54) METHOD OF FORMING AND INCORPORATING A POLYMERIC LENS WITHIN A LENS HOUSING

(71) Applicant: STERIS INSTRUMENT MANAGEMENT SERVICES, INC., Birmingham, AL (US)

(72) Inventor: Peter Pal Bodor, Pembroke Pines, FL (US)

(73) Assignee: STERIS INSTRUMENT MANAGEMENT SERVICES, INC., Birmingham, AL (US)

( * ) Notice: Subject to any disclaimer, the term of this patent is extended or adjusted under 35 U.S.C. 154(b) by 335 days.

(21) Appl. No.: 16/825,824

(22) Filed: Mar. 20, 2020

(65) Prior Publication Data
US 2021/0291468 A1  Sep. 23, 2021

(51) Int. Cl.
*B29D 11/00* (2006.01)
*A61B 1/00* (2006.01)
*B29K 63/00* (2006.01)

(52) U.S. Cl.
CPC ...... *B29D 11/00009* (2013.01); *A61B 1/0011* (2013.01); *A61B 1/00195* (2013.01); *B29D 11/0048* (2013.01); *B29K 2063/00* (2013.01)

(58) Field of Classification Search
CPC .......... B29D 11/00009; B29D 11/0048; A61B 1/0011; A61B 1/00195; A61B 1/002; A61B 1/0009; G02B 23/2423; B29K 2063/00
USPC .................................................. 264/2.2–2.7
See application file for complete search history.

(56) References Cited

U.S. PATENT DOCUMENTS

| | | | | |
|---|---|---|---|---|
| 4,121,896 A | * | 10/1978 | Shepherd | B29D 11/00519 425/808 |
| 5,539,971 A | * | 7/1996 | Kelly | B29D 11/00009 29/418 |
| 7,065,985 B2 | | 6/2006 | Yamanaka | |
| 7,354,536 B2 | | 4/2008 | Hiranuma | |
| 7,561,355 B2 | | 7/2009 | Nakamura | |
| 9,063,265 B2 | | 6/2015 | Matsusue et al. | |
| 9,164,253 B2 | | 10/2015 | Koike et al. | |
| 9,386,909 B2 | | 7/2016 | Fengler et al. | |
| 10,150,689 B2 | | 12/2018 | Cho et al. | |

(Continued)

FOREIGN PATENT DOCUMENTS

| | | | |
|---|---|---|---|
| JP | 2003342024 A | | 12/2003 |
| JP | 2008137336 A | * | 6/2008 |
| WO | 2014/115205 A1 | | 7/2014 |

*Primary Examiner* — Joseph S Del Sole
*Assistant Examiner* — Ariella Machness
(74) *Attorney, Agent, or Firm* — C. Brandon Browning; Ilya S. Mirov; Maynard Nexsen PC

(57) ABSTRACT

A method for forming a lens housing containing a polymeric lens including inserting a mandrel having a distal face with negative features of the desired polymeric lens into a cylinder and filling a reservoir formed between the distal face and a distal end of the cylinder with a curable polymeric lens material. The curable polymeric lens material is cured in place within the reservoir thereby forming the desired polymeric lens. The proximal surface of the polymeric lens is formed and shaped by the distal face of the mandrel, while the distal surface of the polymeric lens is dependent upon the amount of the curable polymeric lens material placed in the reservoir and the volume of the reservoir.

23 Claims, 6 Drawing Sheets

(56) References Cited

U.S. PATENT DOCUMENTS

| | | | |
|---|---|---|---|
| 2002/0159027 A1* | 10/2002 | Tai | B24B 9/146 351/159.19 |
| 2006/0198034 A1 | 9/2006 | Shikano et al. | |
| 2009/0295003 A1 | 12/2009 | Noro et al. | |
| 2010/0127412 A1* | 5/2010 | Lake | B29D 11/00375 264/1.38 |
| 2016/0016837 A1 | 1/2016 | Ogura | |
| 2017/0017018 A1 | 1/2017 | Chao et al. | |
| 2017/0131512 A1 | 5/2017 | Canon | |
| 2019/0282070 A1 | 9/2019 | Vilhelmsen et al. | |
| 2021/0170703 A1* | 6/2021 | Jenkins | B29D 11/00403 |

\* cited by examiner

METHOD OF FORMING AND INCORPORATING A POLYMERIC LENS WITHIN A LENS HOUSING

TECHNICAL FIELD

The present invention is directed to a method of making a polymeric lens and, more particularly, to a polymeric lens formed in place within a lens housing.

BACKGROUND OF INVENTION

A lens or lens system can be used within a device to disperse or focus a light beam depending on the intended function of the device. Examples of such devices that incorporate a lens or lens system include microscopes, cameras, telescopes, and medical devices, such as endoscopes. When constructing these lens-enabled devices, the lens is typically formed in a first step apart from the device and then later positioned and fixed within the device in at least one separate and additional step. For a glass lens, the first step often includes grinding and polishing to produce the lens, while a plastic lens is generally formed by molding the lens using techniques such as injection molding. In each case, a second step is required to glue or mold the lens into the device.

The secondary placement and fixation steps to incorporate lens into devices can, however, add to manufacturing costs and time, as well as introduce alignment errors to the device that can impact device performance. In the present disclosure, methods and systems of simultaneously forming a lens and permanently fixing the lens in its intended housing in a device are presented that utilize a single step. This step encompasses both lens formation and fixation thereby reducing costs and saving time while allowing for more predictable and precise lens alignment within the device.

SUMMARY OF THE INVENTION

The present invention is directed to a method of forming and incorporating a polymeric lens. The method includes providing a mandrel with a distal face having negative features of the desired polymeric lens and inserting the mandrel into a lens housing. The lens housing includes an aperture configured to tightly surround the mandrel and a lens curing region with an interior surface configured to adhere to cured polymer. The mandrel is inserted so that the distal face projects into the lens curing region without extending beyond a distal end of the lens housing. A curable polymeric lens material is added to the lens curing region, so that the curable polymeric lens material covers the distal face of the mandrel. The curable polymeric lens material is cured within the lens curing region to form a polymeric lens. After removing the mandrel from the aperture through a proximal end of the lens housing, the polymeric lens remains permanently fixed within the lens curing region of the lens housing.

When the added curable polymeric material is filled to the distal end of the lens housing, the polymeric lens formed after curing has a flat distal surface. When the added curable polymeric material is filled to a level beyond the distal end of the lens housing, the polymeric lens formed after curing has a convex distal surface. When the added curable polymeric material is filled to a level between the distal end of the lens housing and the distal face, the polymeric lens formed after curing has a concave distal surface. In some embodiments, the distal face of the mandrel is concave thereby imparting a convex proximal surface to the lens. In other embodiments, the distal face of the mandrel is convex thereby imparting a concave proximal surface to the lens.

In one aspect of the invention, there is provided a method of manufacturing a polymeric lens-enabled device. The method includes providing a device for desired polymeric lens insertion and a mandrel with a smooth outer surface and a distal face having negative features of the desired polymeric lens. The mandrel is then inserted into a lens housing of the device, where the lens housing has an aperture configured to tightly surround the mandrel and a lens curing region with an interior surface configured to adhere cured polymer. The mandrel is inserted so that the distal face projects into the lens curing region without extending beyond a distal end of the lens housing. A curable polymeric lens material is added to the lens curing region so that the curable polymeric lens material covers the distal face of the mandrel. Curing the curable polymeric lens material within the lens curing region forms a polymeric lens. Removing the mandrel from the aperture through a proximal end of the lens housing leaves the polymeric lens permanently fixed in the lens curing region of the lens housing. In this way, the device incorporates the polymeric lens and becomes a polymeric lens-enabled device. The lens-enabled device is in some embodiments is a light diffuser that covers an illumination fiber bundle at a distal tip of an endoscope. In these embodiments, the endoscope may be a flexible endoscope, a semi-rigid endoscope, or a rigid endoscope.

According to yet another aspect of the invention, there is provided polymeric lens formation system. The system includes a mandrel with a distal face having negative features of the desired polymeric lens, a lens housing with an aperture configured to tightly surround the mandrel and a lens curing region with an interior surface configured to adhere cured polymer, where the lens housing is configured to receive the mandrel so that the distal face projects into the lens curing region without extending beyond a distal end of the lens housing. The system further includes a curable polymeric lens material configured to at least partially fill the lens housing and cover the distal face. Curing of the curable polymeric lens material within the lens housing results in the formation of the polymeric lens having negative features of the distal face, so that the polymeric lens remains permanently in the lens housing when the mandrel is removed from the aperture. In some embodiments, the distal face is convex, while in other embodiments, the distal face is concave.

A further understanding of the nature and advantages of the present invention will be realized by reference to the remaining portions of the specification and the drawings.

BRIEF DESCRIPTION OF DRAWINGS

The present disclosure same can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION OF THE INVENTION

Figure 7:
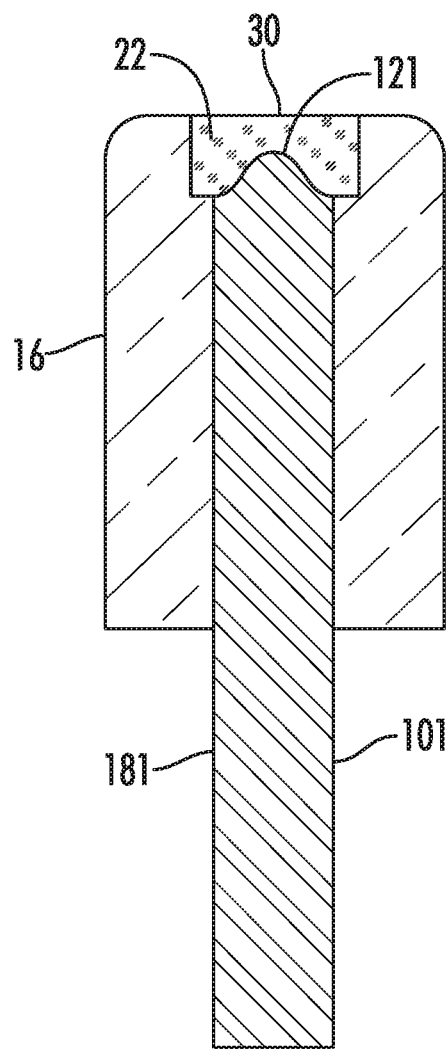
FIG. 7 is a sectional view of a mandrel inserted into a lens housing and a reservoir formed therebetween and containing a volume of a curable, polymeric lens material that is equal to the volume of the reservoir, where the mandrel includes a distal face configured for forming a polymeric lens with an aspherical proximal surface in accordance with a third embodiment of the present invention.
Figure 8A:
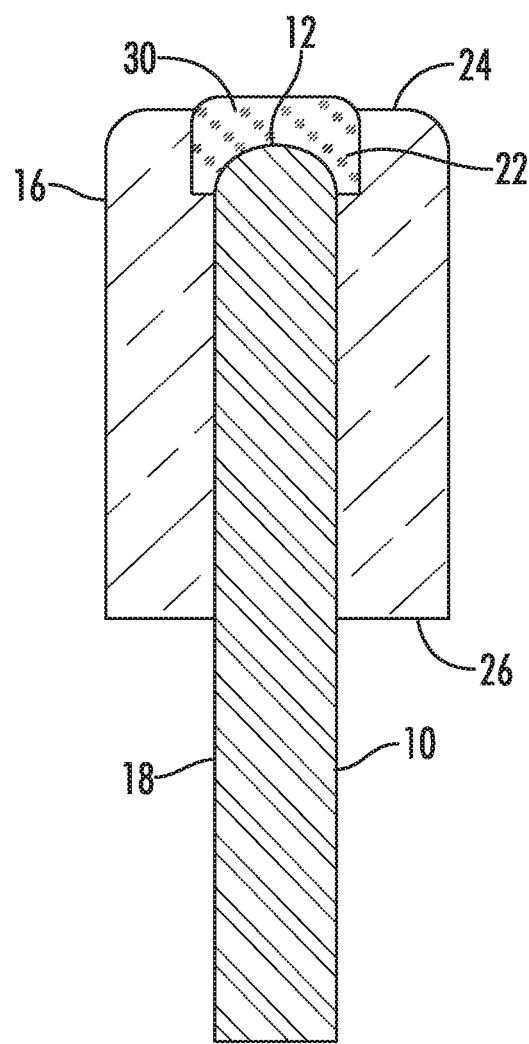
FIG. 8A is a sectional view of a reservoir formed between a lens housing and a mandrel and containing a volume of curable, polymeric material that entirely fills and extends distally beyond a distal end of the lens housing for forming a polymeric lens having a convex distal surface in accordance with a fourth embodiment of the present invention.
Figure 8B:
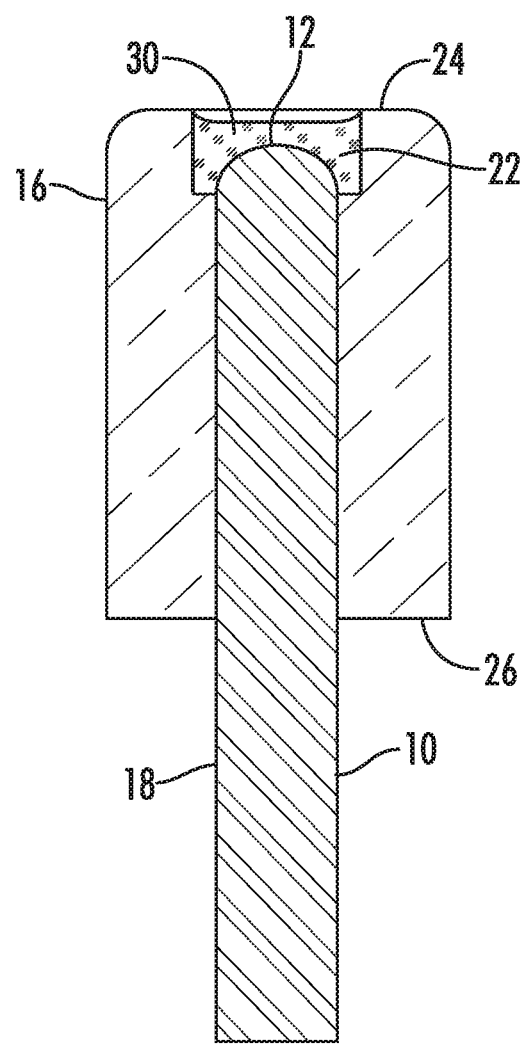
FIG. 8B is a sectional view of a reservoir formed between a lens housing and a mandrel and containing a volume of curable, polymeric material that does not entirely fill the reservoir for forming a polymeric lens having a convex distal surface in accordance with a fifth embodiment of the present invention.

The present invention is directed to methods and systems of forming and incorporating a polymeric lens within a device. FIGS. 1 through 4B depict a first embodiment of the present invention for forming a plano-concave polymeric lens. FIGS. 5 through 6B are directed to a second embodiment of the present invention for forming a plano-convex polymeric lens. FIG. 7 is directed to a third embodiment of the present invention for forming a plano-aspheric lens. FIG. 8A is directed to a fourth embodiment of the present invention for forming a convex-concave polymeric lens, and FIG. 8B is directed to a fifth embodiment of the present invention for forming a bi-convex polymer lens. The system generally includes a lens housing and a mandrel having a distal face with dimensions that serve as a negative to the desired dimensions and features of a proximal surface of the polymeric lens to be formed. The method generally includes inserting the mandrel into the lens housing, adding an optical glue or an epoxy to a reservoir formed between the distal face of the mandrel and the lens housing, curing the glue or epoxy in the reservoir, and thereafter, removing the mandrel from the lens housing. The disclosed methods and systems thus utilize an open-faced mold formed by the lens housing and the distal face.

Figure 1:
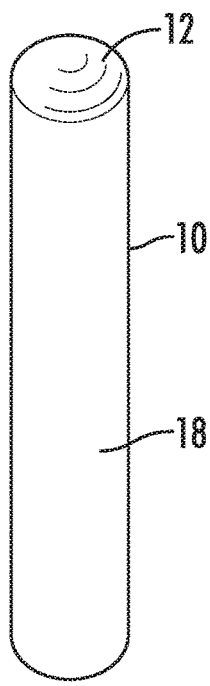
FIG. 1 is a perspective view of a mandrel having a convex distal face in accordance with a first embodiment of the present invention.

Referring to FIG. 1, a mandrel 10 is depicted. Mandrel 10 is fabricated from stainless steel or any other suitable material such that mandrel 10 is moldable into the negative contours of a desired polymeric lens 14 at its distal face 12 and such that mandrel 10 is generally inflexible and configured to have an outer surface 18 that is smooth. The shape of mandrel 10 is compatible with an aperture 20 of lens housing 16, so that distal face 12 is configured to be positioned within aperture 20 at a location where polymeric lens 14 is to be incorporated and fixed. In the first embodiment, mandrel 10 has a modified cylindrical body with a convex distal face 12, though the body of mandrel 10 maybe formed in other shapes not shown. The dimensions, including length, width, and/or diameter of mandrel 10 similarly varies with the corresponding dimensions of aperture 20, so that mandrel 10 fits snugly within aperture 20 with distal face 12 positioned where polymeric lens 14 is to be formed and incorporated. Outer surface 18 of mandrel 10 is prepared so that it is removable from lens housing 16. In some instances, outer surface 18 is highly polished to facilitate removal, while in other instances outer surface 18 is coated with a mold-release material, such as, for example, silicone or polytetrafluoroethylene. Other mold-release materials are contemplated for coating of outer surface 18.

Distal face 12 is designed to include the negative of the dimensions, contours, or other features of the proximal surface of the desired polymeric lens 14. Thus, the dimensions, contours, and features of distal face 12 vary based on the desired polymeric lens, as described in greater detail below.

Figure 2A:
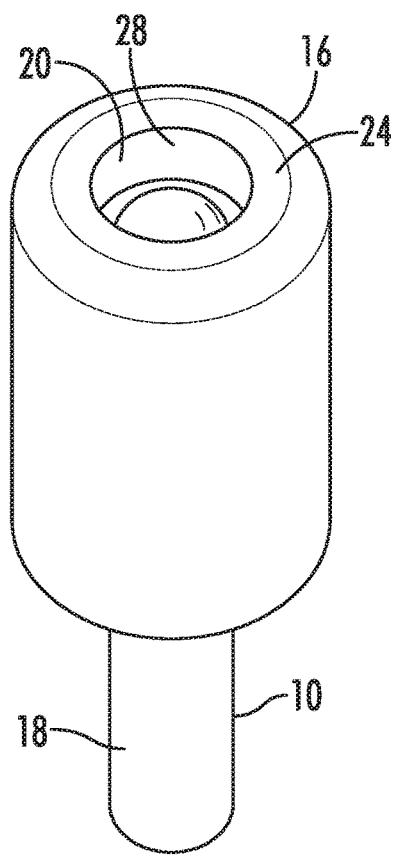
FIG. 2A is a perspective view of the mandrel of FIG. 1 inserted into a lens housing and forming a reservoir therebetween.
Figure 2B:
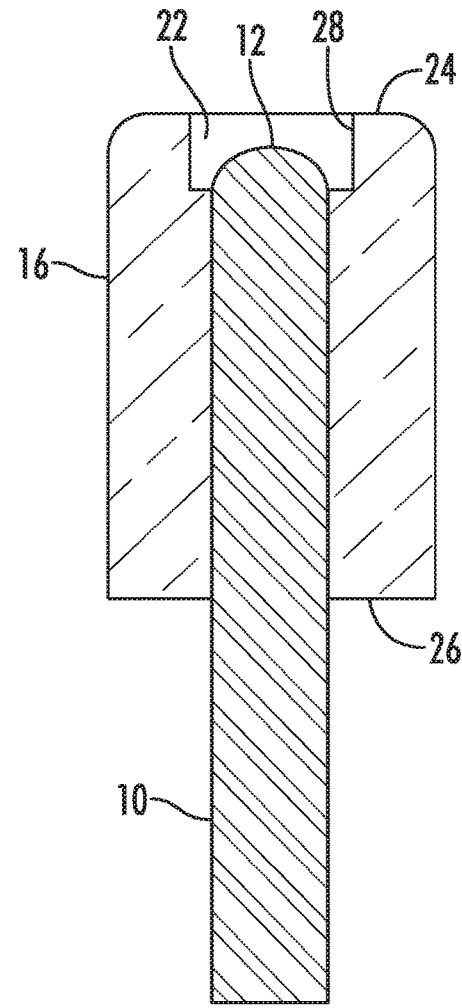
FIG. 2B is a sectional view of the reservoir, mandrel and lens housing of FIG. 2A.

Referring now to FIGS. 2A and 2B, mandrel 10 is inserted into lens housing 16 so that outer surface 18 fits snuggly and tightly within aperture 20. In FIG. 2A, mandrel 10 is shown within aperture 20 of lens housing 16 and positioned so that distal face 12 is within aperture 20. Advancement of mandrel 10 is possible through either distal end 24 or proximal end 26 of lens housing 16. However, in other embodiments not shown, mandrel is advanced through only distal end 24 or proximal end 26 due to device 32 or lens housing 16 geometries. Aperture 20 is circular in cross section in the depicted embodiment, but is potentially shaped differently in other embodiments. However, the cross section of mandrel 10 is designed so that it is shaped to match the cross section of aperture 20 and so that mandrel 10 is configured to be advanced through aperture 20 without substantial aid from specialized equipment.

In FIG. 2B, mandrel 10 is shown as positioned with its distal face 12 in a reservoir or lens curing region 22 of lens housing 16. Distal face 12 is positioned so it does not extend beyond distal end 24 of lens housing 16 and so that the curved portions of distal face 12 are entirely within lens curing region 22. In the depicted embodiment, lens curing region 22 is wider than aperture 20, though in other embodiments it is potentially of equal width or more narrow than aperture 20. The depth of lens curing region 22 from distal end 24 varies depending on the dimensions of lens housing 16, the contours of distal face 12, and the desired thickness of polymeric lens 14. Lens curing region 22 is typically circular in cross section, though its cross sectional shape varies based on the desired dimensions of polymeric lens 14. An inner surface 28 of lens curing region 22 is configured for curing polymer to adhere thereto by having walls that present an adhesive primer coating or are roughened. Additionally, region 22 may include an annular groove that extends radially outward thereby forming a volume into which the polymeric material may flow and form an annual ring within the annular groove, the annular ring resisting removal of the lens from the housing. Thus, as the polymer cures within lens curing region 22, the polymer adheres to inner surface 28 but not to distal face 12.

Figure 3A:
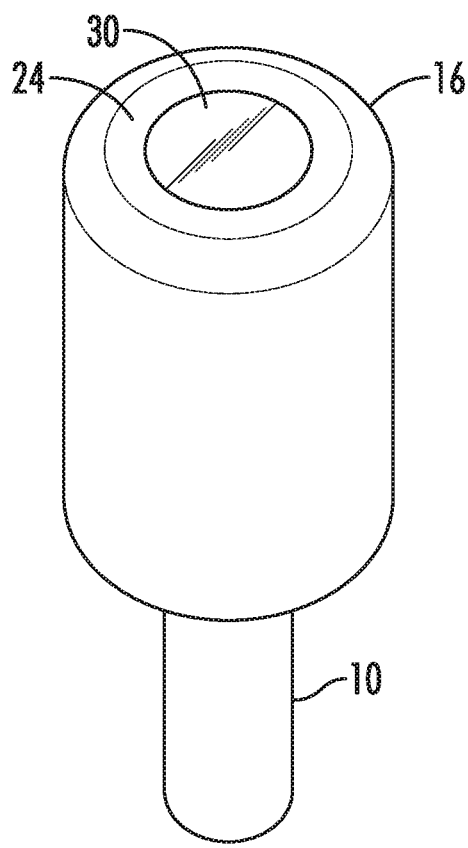
FIG. 3A is a perspective view of a curable, polymeric material located within the reservoir of FIG. 2A, where the volume of the curable, polymeric material is equal to the volume of the reservoir.
Figure 3B:
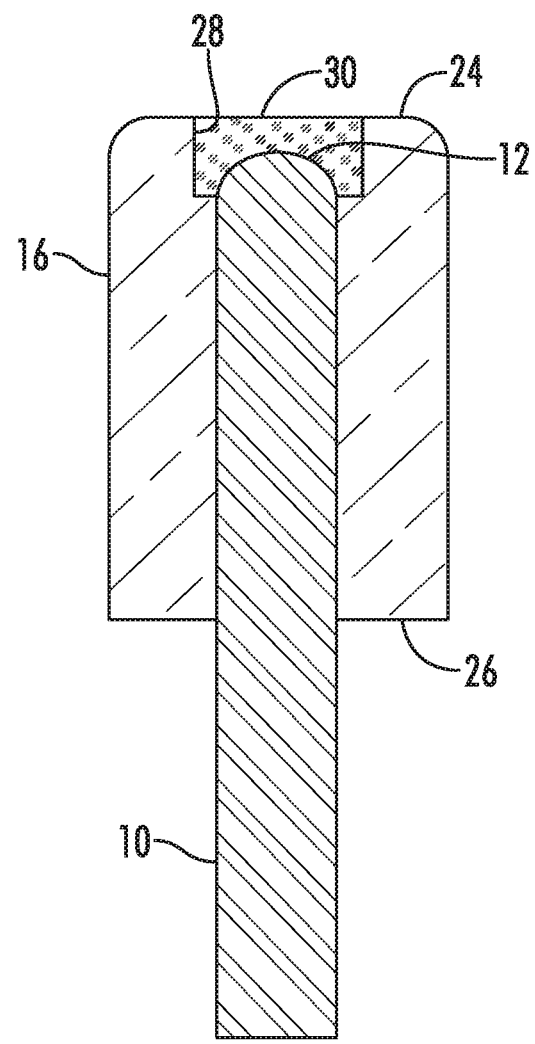
FIG. 3B is a sectional view of the curable, polymeric material located within the reservoir of FIG. 2A.

Now referring to FIGS. 3A and B, a curable polymeric lens material 30 is added to lens curing region 22 after mandrel 10 is inserted and properly positioned. In FIG. 3A, curable polymeric lens material 30 is added through aperture 20 at distal end 24 and enters lens curing region 22. In FIG. 3B, the positioning of curable polymeric lens material 30 is depicted with curable polymeric lens material 30 covering distal face 12 entirely and spreading to meet all walls of inner surface 28. The amount of curable polymeric lens material 30 added varies depending on application and is described in further detail below, though this amount determines the thickness and distal contours of polymeric lens 14. In the depicted embodiment, curable polymeric lens material 30 is contained between distal face 12 and distal end 24 and extends to meet distal end 24 without over-filling or under-filling lens curing region 22.

Curable polymeric lens material 30 is any material that is curable and forms transparent or translucent lens when cured. Thus, examples of curable polymeric lens materials 30 include optical UV glues and optical two-part epoxies. In instances where an optical UV glue is utilized as curable polymeric lens material 30, curing takes place by exposing the added curable polymeric lens material 30 to UV light. In instances where curable polymeric lens material 30 is an optical two-part epoxy, curing takes place by allowing both parts of the epoxy to chemically interact and polymerize, which is potentially expedited or initiated by heating curable polymeric lens material 30 after it is cast. The heating typically takes place in an oven at a temperature determined by the manufacturer of the two-part epoxy, though other temperatures or heating methods are potentially compatible with this method and system. The time of curing is generally determined based on the type of curable polymeric lens material 30 used and the instructions of the manufacturer.

Figure 4A:
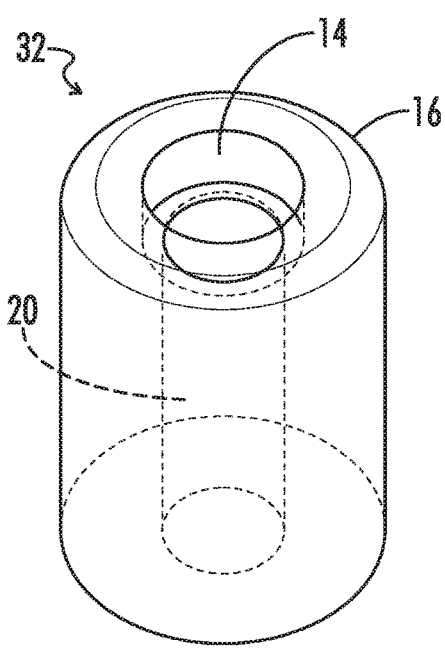
FIG. 4A is a partial sectional view of a polymeric lens formed within the housing of FIG. 2A.
Figure 4B:
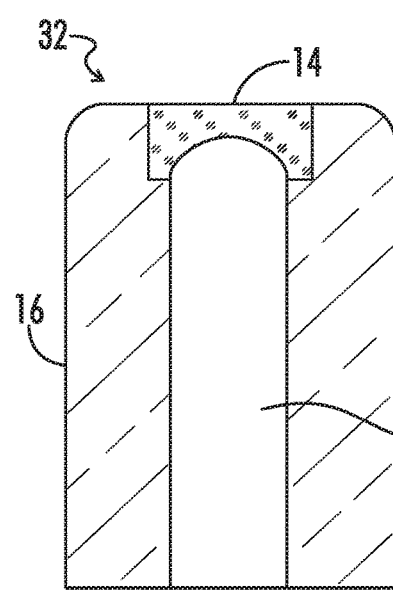
FIG. 4B is a sectional view of the polymeric lens and housing of FIG. 4A.
Figure 5:
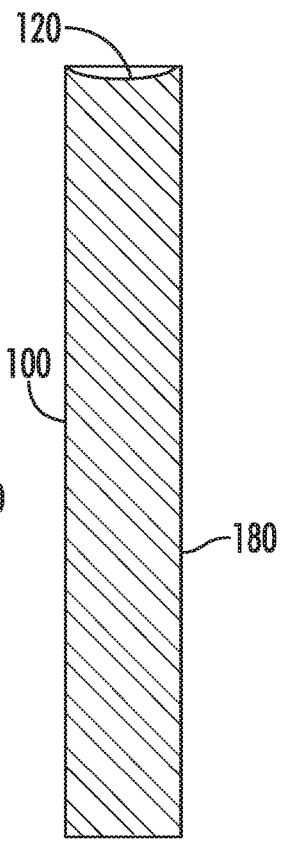
FIG. 5 is sectional view of a mandrel having a convex distal face in accordance with a second embodiment of the present invention.

Referring to FIGS. 4A and B, after the curing of curable polymeric lens material 30, polymeric lens 14 is formed in lens housing 16. The curing step allows liquid curable polymeric lens material 30 to solidify as polymerization occurs, and polymeric lens 14 adheres to inner surface 28 of lens curing region 22 without adhering to distal face 12 of mandrel 10. Thus, mandrel 10 is removable from lens housing 16 without displacing or removing polymeric lens 14. As shown in FIG. 4A, mandrel 10 is removed from proximal end 26 without damage to polymeric lens 14. FIG. 4B shows polymeric lens 14 remaining permanently fixed within lens housing 16 of device 32. The removal of mandrel 10 is possible due to the high polishing or coating with mold-release material of outer surface 18. Polymeric lens 14 adheres to lens curing region 22 due to its inner surface 28 having an adhesive polymer coating or roughened walls. Polymeric lens 14 is at least partially transparent and has a proximal lens face with a negative of the contours or dimensions of distal face 12. The distal lens face of polymeric lens 14, in the depicted embodiment, is planar due to the filling of lens curing region 22 to distal end 24. However, in other embodiments described below, the distal lens face has different contours, dimensions, and/or properties.

Referring to FIG. 5, there is depicted a mandrel 100 having a distal face 120 with a concave shape or contour, which is configured to form a polymeric lens 140 with a convex proximal lens face in accordance with the second embodiment of the present invention. The extent of curvature and depth of the concave region varies based on intended polymeric lens 140 dimensions.

Figure 6A:
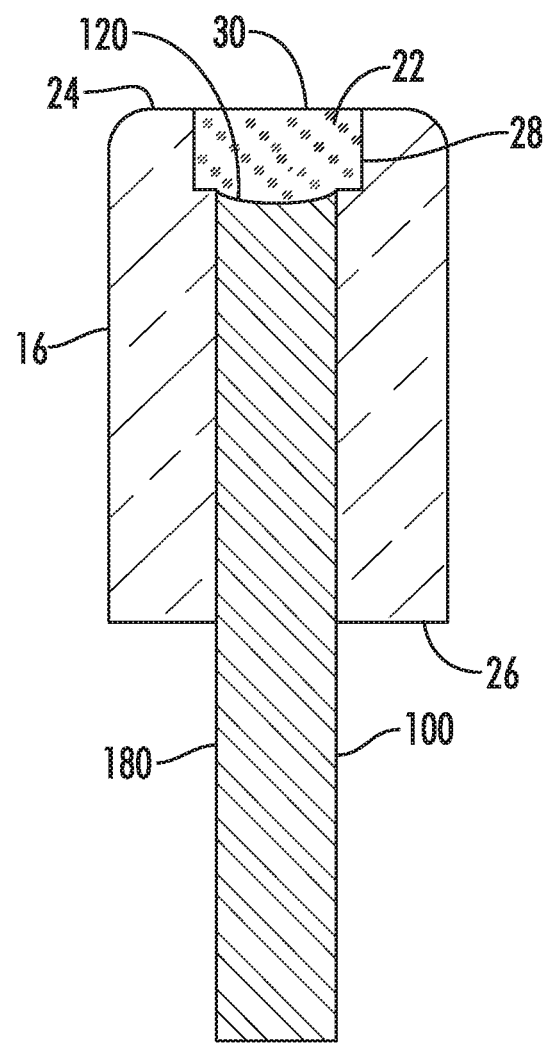
FIG. 6A is a sectional view of the mandrel of FIG. 5 inserted into a lens housing and a reservoir formed therebetween and containing a volume of a curable, polymeric lens material that is equal to the volume of the reservoir.
Figure 6B:
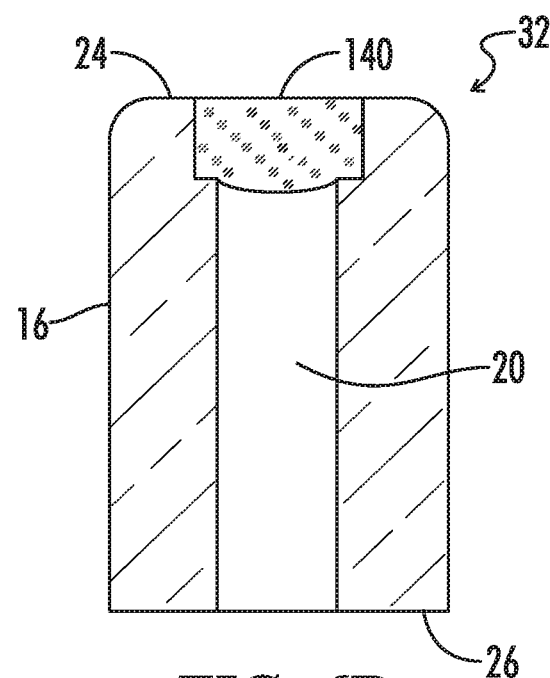
FIG. 6B is a sectional view of a polymeric lens formed within the lens housing of FIG. 6A with the mandrel removed from the lens housing.

In FIGS. 6A and B, mandrel 100 with a concave distal face 120 is used to form and place a convex polymeric lens 140 in lens housing 16. In FIG. 6A, mandrel 100 is inserted into aperture 20 of lens housing 16 and concave distal face 120 is positioned in lens curing region 22. Curable polymeric lens material 30 is added to lens curing region 22 and covers the concave portion of distal face 120 entirely. Additionally, curable polymeric lens material 30 reaches inner surface 28 walls and is filled to a level of distal end 24. Curing occurs while mandrel 100 is in this position, allowing curable polymeric lens material 30 to solidify and polymerize to form polymeric lens 140 in lens curing region 22. In FIG. 6B, mandrel 100 is removed from proximal end 26 of lens housing 16, leaving polymeric lens 140 permanently positioned in lens housing 16. In this embodiment, polymeric lens 140 has a convex proximal lens surface due to the concave distal face 120 of mandrel 100. Further, polymeric lens 140 has a planar distal lens surface because curable polymeric lens material 30 was filled to distal end 24 of lens curing region 22. However, in other embodiments distal lens surface potentially has different contours, dimensions, or properties depending on the amount and level of curable polymeric lens material 30 filled in lens curing region 22.

Referring to FIG. 7, there is depicted a mandrel 101 having a distal face 121 with an aspherical contour in accordance with the third embodiment of the present invention. This embodiment allows mandrel 101 to be inserted in aperture 20 and place the aspherical region of distal face 121 within lens curing region 22 of lens housing 16. Adding curable polymeric lens material 30 to lens curing region 22 and curing this material in lens curing region 22 results in a polymeric lens having a proximal lens surface having contours that are the negative of those of the aspherical contours of distal face 12. Other distal face 12 contours are possible and contemplated for use with the disclosed methods and system.

Now referring to FIGS. 8A and B, the effects of curable polymeric lens material 30 filling level within lens curing region 22 are shown. In FIG. 8A, curable polymeric lens material 30 is over-filled in lens curing region 22. In the depicted example, mandrel 10 has a convex distal face 12, though mandrels with different distal face contours, dimensions, or features, including concave distal faces are contemplated for use with the over-filling of curable polymeric lens material 30 depicted. When curable polymeric lens material 30 is over-filled, the distal surface of curable polymeric lens material 30 forms the shape of the meniscus of curable polymeric lens material 30 due to surface tension properties of curable polymeric lens material 30 in its liquid, un-polymerized form. After curing, curable polymeric lens material 30 forms a polymeric lens with a concave proximal lens surface and a convex distal lens surface. However, in embodiments not depicted, the convex distal lens surface is formed in the aforementioned manner on polymeric lenses 14 with convex or other proximal contours.

In FIG. 8B, curable polymeric lens material 30 is under-filled in lens curing region 22. In the depicted example, mandrel 10 has a convex distal face 12, though mandrel with different distal face contours, dimensions, or features, including concave distal faces are contemplated for use with the under-filling of curable polymeric lens material 30 depicted. When curable polymeric lens material 30 is under-filled, the distal surface of curable polymeric lens material 30 forms the shape of the meniscus of curable polymeric lens material 30 due to surface tension properties of curable polymeric lens material 30 in its liquid, un-polymerized form. After curing, curable polymeric lens material 30 forms a polymeric lens with a concave proximal lens surface and a concave distal lens surface. However, in embodiments not depicted, the concave distal lens surface is formed in the aforementioned manner on polymeric lenses with convex or other proximal contours.

In the aforementioned embodiments and examples, the polymeric lenses are formed, positioned, and affixed into lens housing 16 in a single step. The polymeric lenses have proximal lens surface contours, dimensions, and features that are the negative of those of the distal faces of the mandrels. The polymeric lenses do not require the use of an upper or second mold for the forming of their respective distal lens surfaces. Instead, the amount and level of curable polymeric lens material 30 filled in lens curing region 22 determines the contours and shape of the distal lens surfaces. Changes in curable polymeric lens material 30 surface tension or other material properties potentially impacts the spreading of curable polymeric lens material 30 in lens curing region 22, and different curable polymeric lens materials 30 are potentially selected based on desired material properties for the formation of the lens distal surface.

As will be understood by those familiar with the art, the present invention may be embodied in other specific forms without departing from the spirit or essential characteristics thereof. For instance, the present methods and systems are compatible with lens formation and fixation in various devices, which include but are not limited to microscopes, telescopes, cameras, eyepieces, and medical imaging devices. Additionally, distal faces 12, 120 or 121 of the mandrels 10, 100 and 101, respectively, maybe textured, such that the formed polymeric lenses have corresponding textured inner surfaces for evenly dispersing light. The texturing on the mandrel distal surfaces can be produced by bead blasting, chemical etching, electric discharge machining (EDM) or similar methods. Accordingly, the disclosures and descriptions herein are intended to be illustrative, but not limiting, of the scope of the invention which is set forth in the following claims.

What is claimed:

1. A method of forming a polymeric lens comprising:
   providing a lens housing including a continuous sidewall, a lens curing end, a mandrel insertion end opposite the lens curing end, and a pathway defined by the continuous sidewall and extending to and between the lens curing end and the mandrel insertion end,
   providing a mandrel having a distal face by inserting the distal face through the mandrel insertion end,
   arranging the mandrel within the pathway with the distal face located proximally to the lens curing end of the lens housing thereby forming a reservoir defined by the distal face, the continuous sidewall, and the lens curing end of the lens housing,
   placing an amount of a curable polymeric lens material through the lens curing end of the lens housing opposite the mandrel insertion end and into the reservoir sufficient to cover the distal face of the mandrel, and
   curing the curable polymeric lens material within the reservoir thereby forming the polymeric lens within the lens housing.

2. The method of claim 1, further including removing the mandrel from the lens housing with the polymeric lens remaining permanently fixed to the continuous sidewall.

3. The method of claim 1, wherein the continuous sidewall is configured for adhering to the curable polymeric lens material.

4. The method of claim 1, wherein the distal face of the mandrel is coated with a material configured for preventing adherence of the distal face to the curable polymeric lens material.

5. The method of claim 1, wherein the distal face is convex.

6. The method of claim 1, wherein the distal face is concave.

7. The method of claim 1, wherein the amount of curable polymeric material placed in the reservoir does not entirely fill the reservoir.

8. The method of claim 1, wherein the amount of curable polymeric material placed in the reservoir overfills the reservoir.

9. The method of claim 1, wherein a volume of the amount of curable polymeric material placed in the reservoir is equal to a volume of the reservoir.

10. The method of claim 1, wherein the polymeric lens is selected from the group consisting of a plano-concave lens, a plano-convex lens, a bi-convex lens and a biconcave lens.

11. A method of forming and incorporating a polymeric lens within a lens housing comprising:
    providing a cylinder having a distal end, a continuous sidewall and an inner diameter,
    providing only one rod having a distal face and an outer diameter,
    positioning the only one rod within the cylinder with the distal face located proximally to the distal end of the cylinder thereby forming a reservoir within the cylinder defined by the distal face of the only one rod, the distal end of the cylinder, and the continuous sidewall of the cylinder,
    placing a curable polymeric lens material through the distal end of the cylinder and into the reservoir, wherein the inner diameter of the cylinder and the outer diameter of the only one rod are configured for preventing the curable polymeric lens material from migrating proximally between the cylinder and the only one rod, and
    curing the curable polymeric lens material within the reservoir thereby forming the polymeric lens within the cylinder.

12. The method of claim 11, further including placing an amount of the curable polymeric lens material within the reservoir such that the reservoir is filled to a level distal to the distal end of the cylinder, whereby the polymeric lens is provided with a convex distal surface.

13. The method of claim 11, further including placing an amount of the curable polymeric lens material within the reservoir such that the reservoir is filled to a level proximal to the distal end of the cylinder, whereby the polymeric lens is provided with a concave distal surface.

14. The method of claim 11, further including placing an amount of the curable polymeric lens material within the reservoir such that the reservoir is filled to a level that is coplanar with the distal end of the cylinder, whereby the polymeric lens is provided with a flat surface.

15. The method of claim 11, wherein the distal face has a shape selected from the group consisting an aspherical shape, a concave shape and a convex shape.

16. The method of claim 11, wherein the curable polymeric lens material is selected from the group consisting of an optical glue including a mix of liquid polymer resins which crosslink with each other when exposed to ultraviolet light and an optical two-part epoxy.

17. The method of claim 11, further including coupling the cylinder and the polymeric lens to a distal tip of an endoscope.

18. The method of claim 11, wherein the distal face of the only one rod is textured for imparting a textured surface to the polymeric lens.

19. A method of forming and incorporating a polymeric lens within a lens housing comprising:
providing a cylinder having a continuous inner sidewall, a rod insertion end, and a lens curing end opposite the rod insertion end,
providing only one rod having a distal face by inserting the distal face through the rod insertion end,
positioning the only one rod within the cylinder with the distal face located proximally to the lens curing end of the cylinder thereby forming a reservoir within the cylinder defined by the distal face of the only one rod, the lens curing end of the cylinder and the continuous sidewall,
placing a curable polymeric lens material within the reservoir through the lens curing end of the cylinder opposite the rod insertion end, and
curing the curable polymeric lens material within the reservoir thereby forming the polymeric lens within the cylinder,
wherein a shape of the distal surface of the polymeric lens is not dependent upon a shape of a proximal face of a mold.

20. The method of claim 19, wherein the shape of the distal surface of the polymeric lens is selected from the group consisting of a concave shape, a convex shape and a planar shape wherein, (i) when the concave shape is selected, the reservoir is filled with the curable polymeric lens material to a level proximal to the distal end of the cylinder, (ii) when the convex shape is selected, the reservoir is filled with the curable polymeric material to a level distal to the distal end of the cylinder, and (iii) when the planar shape is selected, the reservoir is filled with the curable polymeric lens material to a level even with the distal end of the cylinder.

21. The method of claim 19, wherein the curable polymeric lens material is introduced within the reservoir through the distal end of the cylinder.

22. The method of claim 1, wherein the mandrel further includes only one mandrel and arranging the mandrel within the pathway further includes forming a reservoir within the cylinder defined by the distal face of the only one mandrel, the continuous sidewall, and the lens curing end of the lens housing.

23. The method of claim 11, wherein:
the distal end of the cylinder is a lens curing end and the cylinder includes a rod insertion end opposite the lens curing end,
providing the only one rod further includes inserting the distal face of the only one rod through the rod insertion end, and
the curable polymeric lens material is placed through the lens curing end.

* * * * *